United States Patent [19]

Barrett et al.

[11] 4,339,825

[45] Jul. 13, 1982

[54] BI-PLANE ANGIOGRAPHIC APPARATUS

[75] Inventors: David M. Barrett; Paul M. Stivender, both of Brookfield; Robert E. Ueberfluss, Greendale, all of Wis.

[73] Assignee: General Electric Company, Schenectady, N.Y.

[21] Appl. No.: 202,093

[22] Filed: Oct. 31, 1980

[51] Int. Cl.³ .............................................. G03B 41/16
[52] U.S. Cl. ................................................... 250/490
[58] Field of Search ............... 250/439 R, 444, 445 R, 250/446, 447, 448, 468, 523, 490, 491

[56] References Cited

U.S. PATENT DOCUMENTS

| | | | |
|---|---|---|---|
| 3,549,885 | 12/1970 | Andersson | 250/523 |
| 3,659,099 | 4/1972 | Bertheau | 250/490 |
| 3,803,418 | 4/1974 | Holstrom | 250/491 |
| 3,892,967 | 7/1975 | Grady | 250/447 |

Primary Examiner—Craig E. Church
Attorney, Agent, or Firm—Ralph G. Hohenfeldt

[57] ABSTRACT

Angiography apparatus has an L-arm rotatable about a vertical axis and a U-arm mounted on the upstanding section of the L-arm for rotation about a horizontal axis. An X-ray source is at one end of the U-arm and image receptors including an image intensifier and a first film changer are at the other end to enable making posterior-anterior and anterior-posterior X-ray views at various angles relative to a patient who is located on the isocenter which is the intersection of the horizontal, vertical and X-ray beam axis. A second film changer for making lateral generally isocentric views is mounted within the U-arm on a stand that is movable along the horizontal U-arm axis to allow obtaining various distances between the image plane of the film and another X-ray source. The lateral changer is on a mechanism for shifting it vertically and longitudinally a limited amount and for rotating it with a motor so this changer will stay level until the U-arm has been tilted through a predetermined angle. After this angle is reached motorized rotation is discontinued and the lateral changer is allowed to rotate with the U-arm.

12 Claims, 8 Drawing Figures

BI-PLANE ANGIOGRAPHIC APPARATUS

BACKGROUND OF THE INVENTION

This invention pertains to X-ray apparatus and, in particular to apparatus that is adapted for angiography.

In angiography procedures it is frequently necessary to obtain X-ray views of the blood vessels in two different directions simultaneously such as in the postero-anterior (PA) direction and in the lateral direction, that is, substantially orthogonal to the PA direction. Apparatus which permits making AP and even postero-anterior (PA) views is presently available. Customarily, the apparatus may have an X-ray source mounted on an arm of a supporting gantry and one or more image receptors, such as an X-ray image intensifier and a rapid radiographic film changer, on another arm spaced from the X-ray source. The gantry provides for positioning the source and receptors at various angles with respect to a patient who is supported on a table between the source and receptors.

When a lateral view is to be taken with prior art apparatus, an X-ray source which is usually mounted overhead or being moved along three orthogonal axes, is positioned next to the patient for directing the X-ray beam to a floor-mounted rapid film changer. Thus, as is well known, the floor-mounted film changer and its associated electrical cables interferes with movements of the physician around the patient and it may also prevent positioning the source and receptor for PA views at certain desired angles relative to the patient.

SUMMARY OF THE INVENTION

In accordance with the invention, a gantry which supports an X-ray source and a first film changer for making PA views, has a second rapid film changer mounted directly on it above the floor level and out of the path of the axis of the X-ray beam running from the X-ray source on the gantry to the first film changer. The second film changer is located in the gantry such that another triaxially movable overhead supported auxiliary X-ray tube can be positioned next to the patient for directing its beam toward the second film changer. Hence, the second film changer is always off the floor and in a position which permits lateral X-ray views to be taken regardless of how the physician might have the gantry angulated and oriented with respect to one part or another of the patient's body.

Further, in accordance with the invention, the second film changer is mounted in a manner which permits it, that is, its image plane to be located relatively far from the patient for obtaining X-ray views having magnification and for being located close to the patient for obtaining views with minimum magnification contact views. The arrangement provides for obtaining a constant X-ray source-to-image distance (SID) for lateral X-ray views if desired by moving the second film changer and auxiliary X-ray source corresponding distances relative to the stationarily supported patient. The SID can be conveniently varied which is desirable in connection with angiographic procedures. Since the support system for the second or lateral film changer is integral with the gantry, the lateral film changer moves through space with no unexpected equipment interference. Movement of the film changer mount axially away from the patient and isocenter to the extreme of its travel provides a large amount of clearance for those procedures wherein the lateral film changer is not in use.

Briefly stated, the multiaxial angiographic apparatus with which the new adaptation for bi-plane imaging is illustrated comprises an L-Shaped arm (called the L-arm) whose long leg is fastened to a floor-mounted bearing for rotation about a vertical axis. The short leg of the L-arm extends vertically upwardly from the long leg. A U-shaped arm assembly is mounted for rotation about a horizontal axis on the upstanding leg of the L-arm. The U-arm comprises a base section whose midpoint coincides with the horizontal rotational axis and it has a pair of leg sections extending from opposite ends of the base section and on opposite sides of the axis. A radially movable image intensifier and a radially movable first rapid film changer are mounted at the end of one of the leg sections and an X-ray source is mounted to the end of the other leg section for projecting a beam along an axis that intersects the input plane of either the image intensifier or the film changer depending on whether or not the film changer has been advanced to active radiographic position. By rotating the L-arm about the vertical axis and the U-arm about its horizontal axis, the U-arm and, hence, the X-ray source and intensifier and changer image receptors can be aligned at a multiplicity of angles relative to a patient who is being supported supinely on a table between the legs of the U-arm for enabling AP views to be made. The patient is supported in coincidence with an isocentric point which is the point of intersection of the vertical L-arm axis, the horizontal U-arm axis and the axis of the X-ray beam.

In accordance with the invention, a second film changer for making lateral X-ray views is mounted between the leg sections of the U-arm on a carriage which permits the second film changer to be positioned at selected distances relative to the patient. The horizontal axis of the U-arm extends perpendicularly through the vertically oriented film or imaging plane of the second film changer so the second film changer is aligned with the isocenter too.

The second film changer is on a mounting which permits its longitudinal axis to be rotated oppositely of U-arm rotation so the changer can be optionally held in a preferred horizontal orientation manually or automatically for most procedures and the mounting is provided with means for letting the second film changer rotate in the same direction about the horizontal axis through a limited angle to avoid having the second film changer collide with the first changer when the U-arm is angulated beyond a certain angle. The mounting also provides for shifting the second film changer longitudinally and vertically by a small amount to enable clearing the shoulder of the patient when it is desired to put the film changer near or in direct contact with the patient's head, for example.

The manner in which the X-ray apparatus with two integrated film changers is implemented will now be described in greater detail in reference to the drawings.

DESCRIPTION OF THE DRAWINGS

FIG. 6 is a section taken on a line corresponding with 6—6 in FIG. 3 with some parts omitted;

FIG. 7 is a fragmentary plan view of the head portion of a patient who is supine on an X-ray transmissive table top with the lateral film changer shifted longitudinally for clearing the patient's shoulder to enable lateral low magnification radiography of the head; and FIG. 8 is a diagrammatic front view of the apparatus for illustrating how the lateral film changer can be rotated to avoid interference by the components carried by the U-arm when the arm is rotated beyond a predetermined angle.

DESCRIPTION OF A PREFERRED EMBODIMENT

Figure 1:
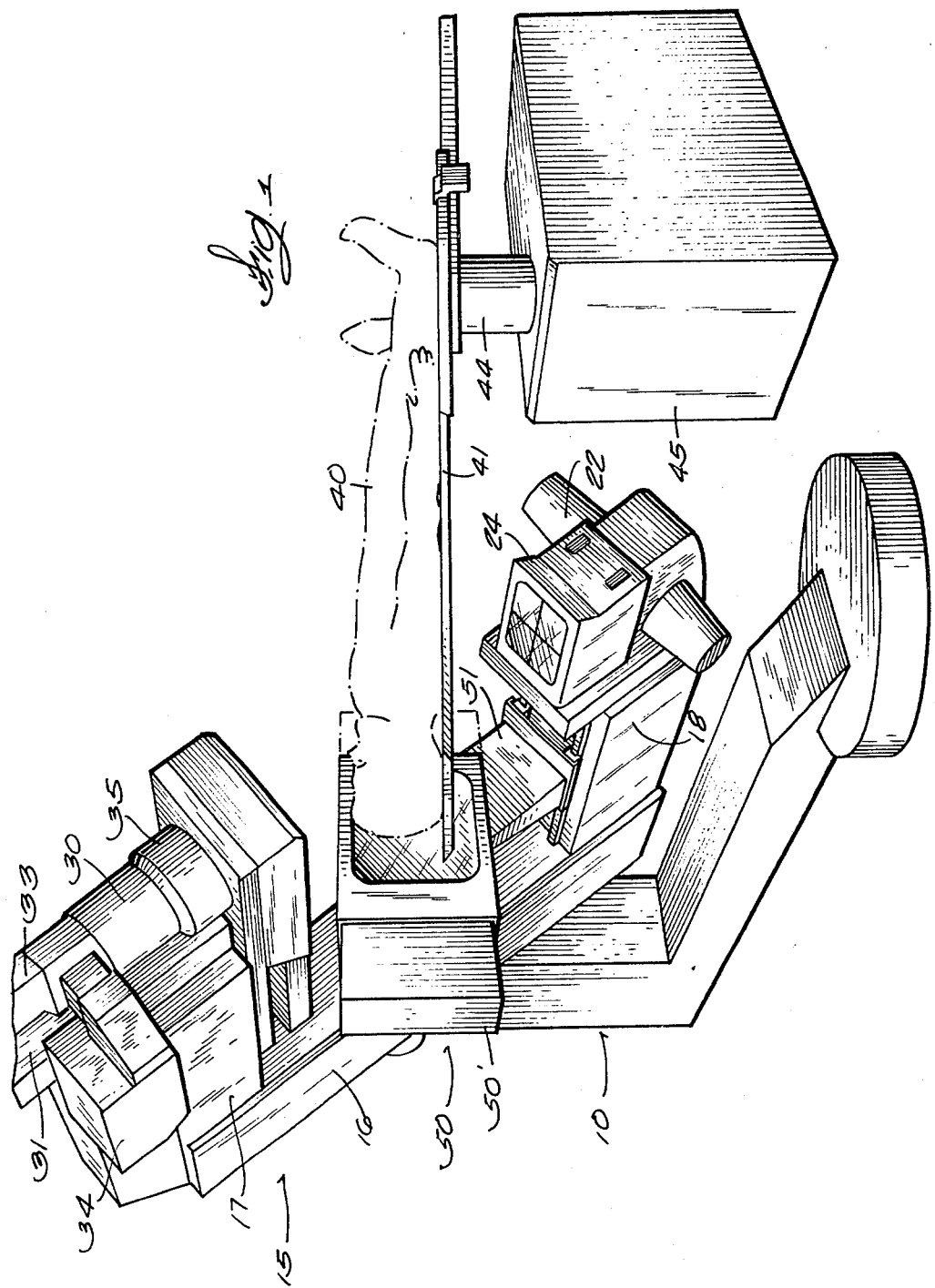
FIG. 1 is a perspective view of X-ray apparatus adapted for bi-plane angiography, this FIGURE showing the U-arm angulated from vertical for making a PA view, that is, where the X-ray source is posterior to the patient and one cooperating image receptor is anterior to the patient.
Figure 2:
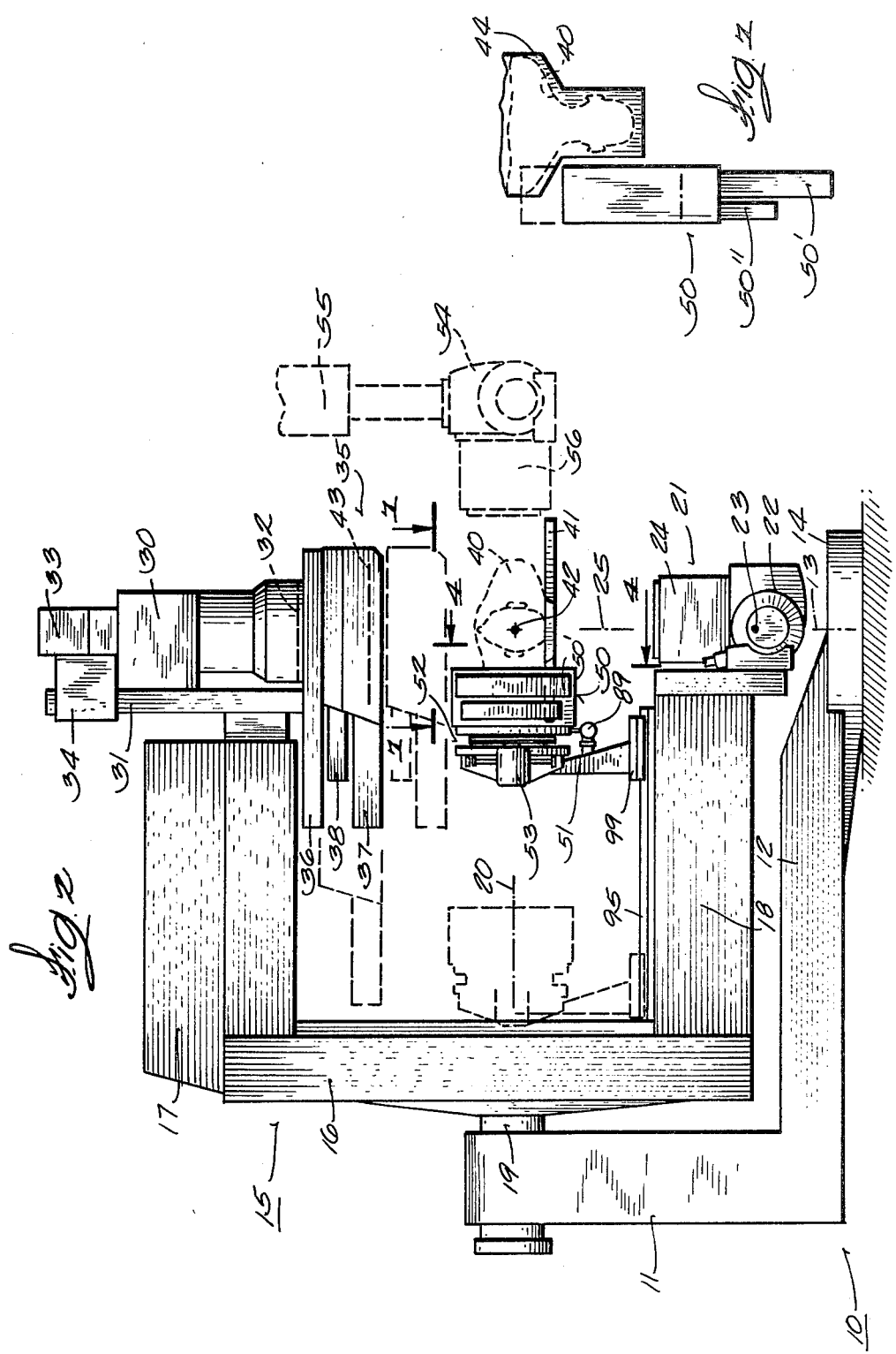
FIG. 2 is a side elevation view of the apparatus taken when the U-arm is rotated to its vertical attitude and showing the first film changer, depicted in solid and phantom lines, positioned for PA radiography and the second film changer positioned close to a patient's head for making lateral and low magnification or true projection radiographic views.

FIGS. 1 and 2 facilitate providing a general description of the apparatus. It comprises a rotatable support in the form of an L-arm, generally designated by the numeral 10, and composed of an upstanding or vertical leg 11 and a horizontal leg 12 which is journaled for rotation about a vertical axis 13 in a floor-mounted bearing 14. The rotatable support could be mounted overhead as long as it provides for rotation about a vertical axis. A generally U-shaped arm, called a U-arm assembly is designated generally by the reference numeral 15 and, for the sake of convenience, is characterized as being comprised of a base member 16 and axially extending and radially spaced apart leg members 17 and 18, respectively. At about its midpoint, the U-arm has a shaft 19 which is journaled for rotation, in the upper end of the L-arm leg 11, about a horizontal axis indicated by the numeral 20.

An X-ray source assembly, generally designated by the numeral 21 is mounted to the end of U-arm leg member 18. The X-ray source assembly comprises an X-ray tube casing 22 which contains an X-ray tube, not visible, whose focal spot 23 lies in a vertical plane that is perpendicular to the plane of the drawing in FIG. 2. The focal spot is the actual source of the X-ray beam. An X-ray beam boundary defining collimator 24 of known type is coupled to the X-ray tube casing. The central X-ray or axis of the X-ray beam emanating from the focal spot is indicated by the dash-dot line marked 25. The X-ray beam axis 25 is coincident with the vertical rotational axis 13 of the L-arm 10.

At the outer end of U-arm leg 17, an X-ray image intensifier 30 is mounted on a carriage, not visible, that is mounted on another carriage 31 such that the image intensifier may be moved from the radially outermost position in which it is shown radially inwardly with respect to horizontal rotational axis 20 of the U-arm. The image plane of the intensifier is represented by a dashed line 32. The upper end of the intensifier has a housing 33 for a video camera and another housing 34 for a 105 mm high speed camera, neither of which cameras are visible.

An automatic rapid film changer 35 is mounted adjacent the image intensifier. A suitable film changer is one sold under the name "Puck", this changer being widely used and well known in the X-ray industry and is available from Elema-Schonander, Inc. Typical film changer 35 has two removable magazines, one of which, 37, stores unexposed films and the other of which, 38, receives and stores films after they have been exposed. The film changer 35 is indirectly mounted to the radially movable carriage 31 which enables the film changer to be moved radially with respect to horizontal U-arm axis 20 from the solid line position in which it is depicted in phantom lines. The film changer 35 is mounted to a support 36 which is translatable on the radially movable carriage 31 so as to be able to retract the film changer from its active position in alignment with the X-ray source axis 25 to an inactive or parked position close to the base of the U-arm where it is depicted partially in phantom lines.

The patient 40 undergoing examination is arranged supinely on an X-ray transmissive table top 41. As can be seen in FIG. 2, the patient is at the level of the isocenter of the system which is the point 42 of intersection of the vertical L-arm axis 13, the X-ray beam axis 25 and the horizontal U-arm axis 20. The X-ray beam axis passes through the center of the image intensifier image input plane 32 and, when the changer is in active position, through its film plane 43, indicated by a dashed line in film changer 35. More details on the gantry comprised of an L-arm and a U-arm and more details on the manner in which the image intensifier and film changer are carriage mounted may be seen in copending application Ser. No. 202,094 filed 10-31-80, which is incorporated herein by reference.

The structure which has been described thus far, that is, the combination of an L-arm, a U-arm, an image intensifier and a film changer and an X-ray source mounted on the U-arm for making PA X-ray views at various angulations relative to a patient may be considered to be known for present purposes and as providing the basis for the new lateral radiography adaptation which will be discussed in detail shortly hereinafter.

As depicted in FIGS. 1 and 2, the U-arm is angulated or positioned at the present time for PA imaging, that is, where the X-ray source is at the back of the supine patient and one or the other receptors, that is, the film changer or image intensifier is at the front. By rotating the L-arm on its axis and the U-arm on its axis, various angular PA views of the patient's blood vessels and surrounding anatomy may be obtained. As illustrated in FIG. 1, the X-ray table top 41 is supported in cantilever fashion on a vertically movable column 44 extending from a housing 45 which has a mechanism, not shown, for raising and lowering the column to make it easier for the patient to be put on or taken off of the table top. In the described system, however, the patient is maintained at the level of the isocenter 42 for almost all procedures. The table top 41 is also mounted on the column for being slid horizontally.

Now that the preexisting part of the apparatus has been described in sufficient detail, the new arrangement for making lateral X-ray views with a film changer that is integrated into the L/U-arm or gantry will be described.

Referring to FIG. 2, the lateral film changer is designated generally by the reference numeral 50. This film changer is structurally and functionally similar to the PA film changer 35. It includes an unexposed film magazine 50′ and an exposed film magazine 50″ as can be seen clearly in FIG. 7. Film changer 50 in FIG. 2 is mounted on a stand or upright member 51 which is translatable on axially extending U-arm leg section 18 for disposing the film in this changer at various selected distances from the patient. The film changer is mounted on a mechanism 52 which facilitates limited rotation of the film changer about horizontal U-arm axis 20 under certain circumstances and also facilitates limited longitudinal and vertical movements of the film changer with respect to stand 51 as will be explained in detail shortly hereinafter. Changer 50 is depicted truly horizontal in FIGS. 1 and 2 since this is its attitude for most procedures. Limited rotation of the film changer is obtained with a motor 53 which can be seen in FIG. 2 but vertical and longitudinal translation of film changer 50 are achieved with hand operated lead screws which are omitted from FIG. 2 although they are shown in detail in other views and will be described later.

Still referring to FIG. 2, longitudinal movement of the film changer 50 is defined as movement generally in parallelism with the floor and the longitudinal axis of the film changer is defined as being perpendicular to the plane of the drawing in FIG. 2 where the U-arm happens to be in its vertical position. The longitudinal axis in FIG. 1 would be a line drawn horizontally across the center of the film changer. Vertical movement of the film changer 50 is defined as movement along the line of the U-arm base section 16 regardless of where the U-arm 15 is angulated about axis 20.

As can be seen in FIG. 2, lateral X-ray views of the patient 40 are obtained with an auxiliary X-ray source 54 which is mounted on a vertically telescoping support 55. Support 55 may be considered to be mounted on an overhead crane, not shown, for being moved along orthogonal x, y and z axes. A collimator assembly 56 is coupled to X-ray tube casing 54 for defining the X-ray beam which is projected laterally through the patient to form an image on a radiographic film in film changer 50. The rotational axis of the film changer usually passes through isocenter 42.

The mounting structure for the lateral film changer 50 will now be described in greater detail in reference to FIGS. 3-6 primarily.

Figure 3:
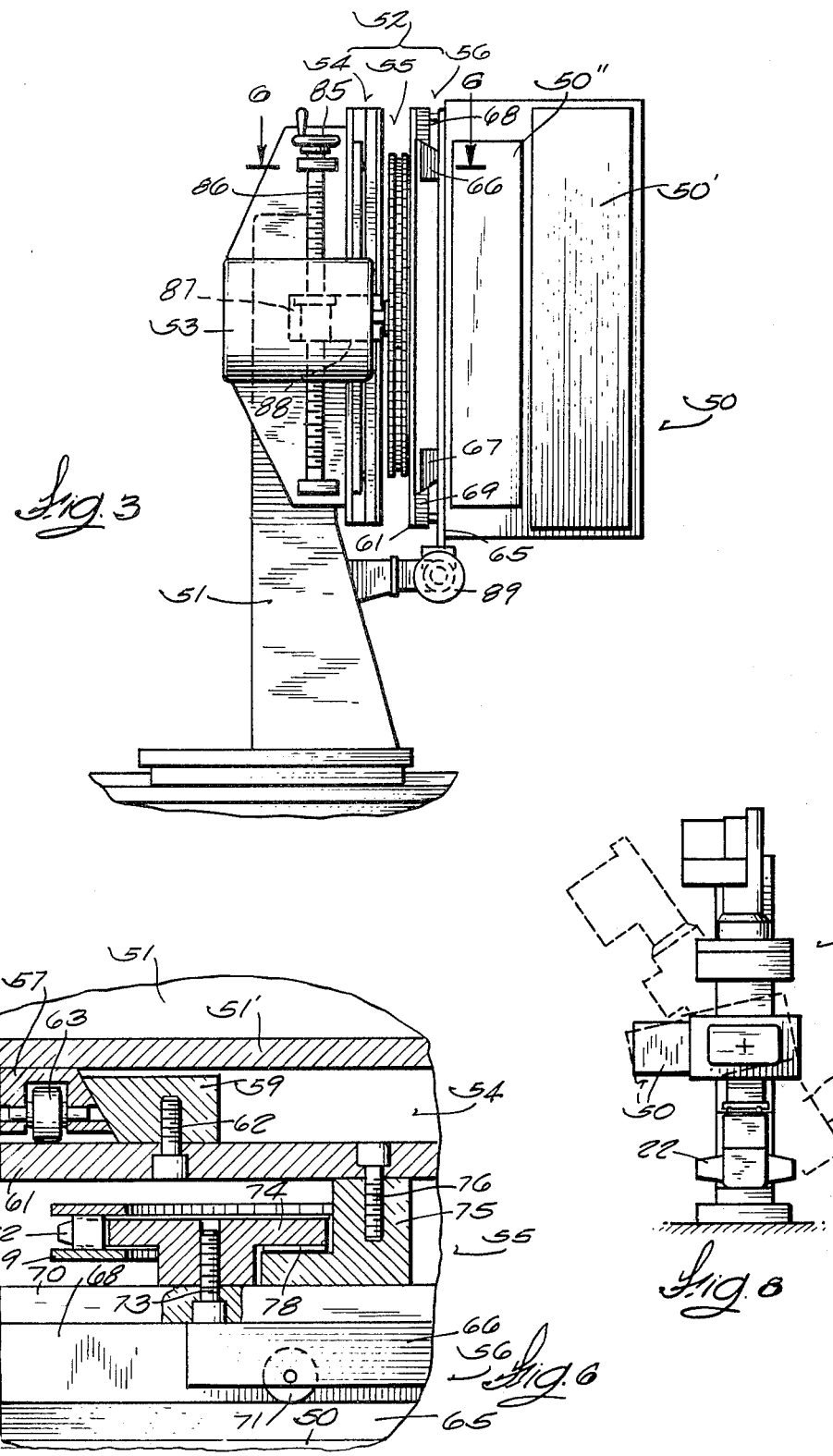
FIG. 3 is a side view of the second or lateral film changer and its supporting mechanism isolated from the complete FIG. 1 and 2 embodiments.

As can be seen in FIG. 3, rotate and translate mechanism 52 is comprised of three major subassemblies 54, 55 and 56. FIG. 6 shows the essential details of these subassemblies which are interposed between stand 51 and film changer 50. The components for enabling limited vertical movement of the film changer 50 relative to stand 51 include a pair of generally vertically directed beveled tracks 57 and 58 whose end view can be seen in FIG. 5. Tracks 57 and 58 are fixed to stand 51 by reason of their being fastened to plate 51′ which is fastened to the stand. The tracks are engaged in complementary fashion with beveled guides 59 and 60. One of the tracks 57 and its cooperating guide 59 are shown enlarged and in section in FIG. 6. Typical guide 59 in FIG. 6 is clamped to a plate 61 by means of machine screws such as the one marked 62. Rollers such as the one marked 63 are provided for reducing friction. It will be evident that plate 61 is constrained to move vertically only where vertical is perpendicular to the plane of the drawing in FIG. 6.

Figure 4:
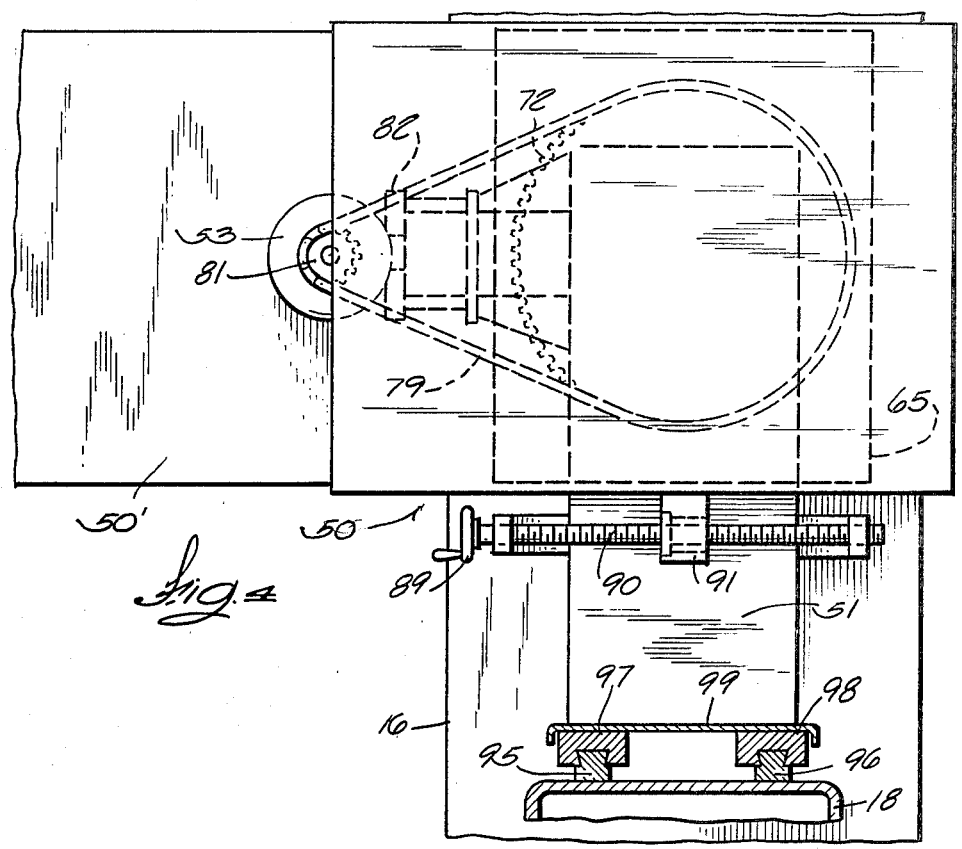
FIG. 4 is a front elevation view of the lateral film changer, partly in section, taken on a line corresponding with 4—4 in FIG. 2.
Figure 5:
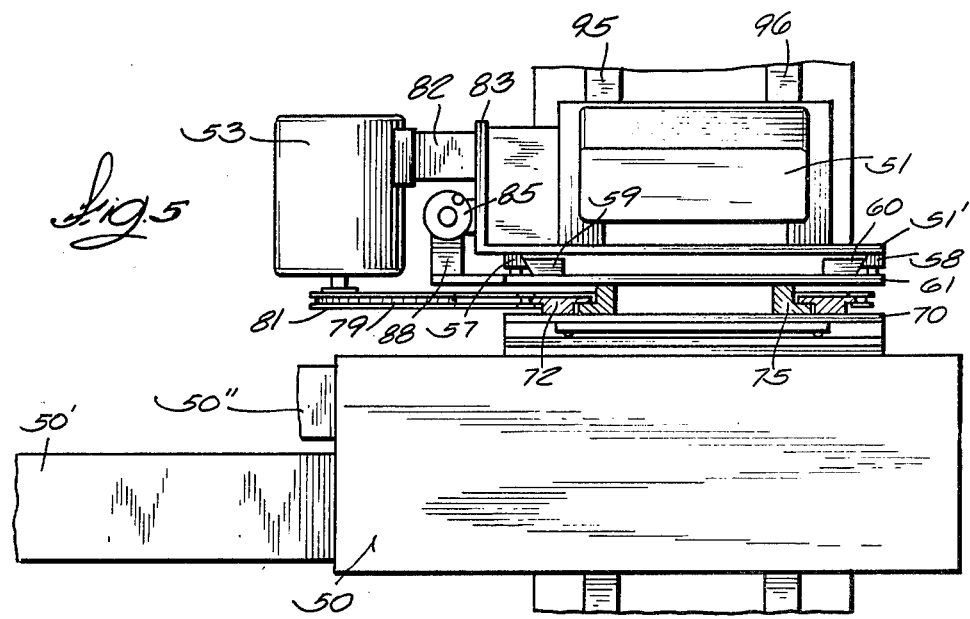
FIG. 5 is a top view of the mechanism shown in FIG. 4 with some parts broken away.

The subassembly 56 is for enabling the film changer 50 to be shifted by a limited amount longitudinally and is similar to the mechanism just described for vertical movement except that the mechanism for longitudinal movement is disposed or rotated 90° with respect to the vertical movement mechanism. Thus, as can be seen in FIGS. 3 and 6, there is a plate 65 to which the film changer 50 is fastened. Beveled guides 66 and 67 are fastened to plate 65 and complementary bevel tracks 68 and 69 are fastened to a plate 70. Rollers such as the one marked 71 are also provided. It will be evident that plate 65 and film changer 50 which it carries are constrained to move longitudinally, that is, parallel to the plane of the drawing sheet in FIG. 6 relative to plate 70. Plate 70 has a ring-shaped sprocket 72 fastened to it by means of a circular array of machine screws 73. As can be seen in FIG. 6, sprocket 72 has a radially inwardly extending rim 74 which overhangs a ring 75 which is L-shaped in cross section and is fastened to plate 61 of the vertical movement subassembly by means of a circular array of machine screws such as the one marked 76. The complementary shapes of rim 74 on the sprocket and the L-shaped ring 75 result in a circular bearing being created at the interfacing surfaces 78. A chain 79, one link of which is visible in FIG. 6, is used for applying a rotational force to sprocket 72. When the sprocket is driven rotationally, the outer normally horizontal subassembly 56 and the film changer 50 mounted thereon rotate on bearing 78. FIGS. 4 and 5 show clearly how ring sprocket 72 is driven by means of chain 79 through the agency of a motor 53 which has a sprocket 81 on its shaft. The motor is mounted on a bracket 82 which is fastened to a part 83 which is mounted on upright stand 51.

As shown in FIG. 1, film changer 50 is presently horizontal, that is, it has its long axis or dimension parallel to the floor even though the U-arm has been angulated away from vertical. Horizontal is the normal attitude of the film changer. It is maintained horizontal when the U-arm is turned in either direction away from vertical by driving it with motor 53 in a direction opposite to the direction in which the U-arm is angulated from vertical.

In the illustrated embodiment, as one may infer from FIG. 1, interference could occur between film changer 35 and lateral film changer 50 after the U-arm is rotated about 40° from vertical. Thus, to avoid the consequences of an interference, counterrotation of the film changer 50, described in the preceding paragraph, is discontinued when the U-arm is at about 40° from vertical in which case the film changer 50 simply turns with the U-arm 15 and departs from its normal horizontal attitude. In an actual design, about 10 more degrees of U-arm rotation is permitted in the way. The motor controls for achieving these functions are not shown nor discussed since they can be devised by an electrical designer using level sensing devices and relays by way of example. FIG. 8 shows the U-arm 15 in phantom lines where it has been rotated in one of its directions from vertical more than a predetermined angle, such as 40°, in which case the lateral film changer 50, also in phantom lines, is now rotating with the U-arm since counterrotation to keep it in its solid line position has been discontinued.

Film changer 50 is movable vertically to a limited extent through the agency of subassembly 54 that uses a hand wheel 85 which turns a lead screw 86 as can be seen particularly well in FIGS. 3 and 5. The lead screw turns within an internally threaded nut 87 that is coupled by means of a bracket 88 to plate 61 in the vertical movement subassembly. In an actual embodiment, provision is made for raising and lowering the film changer 50 about 4 inches but this is only for certain procedures as will be explained. Normally, however, the center of the image plane in the film changer is held in coincidence with the horizontal axis 20 of the U-arm.

Movement of the film changer longitudinally a short distance, for example, about 4 inches in an actual embodiment, is accomplished by turning another hand wheel 89 which, as can be seen in FIG. 4, turns a lead screw 90 that is engaged in a nut 91. The nut is fastened to plate 65 on which the film changer 50 is mounted. As is evident from inspection of FIG. 3, turning of the lead screw will cause the film changer to move longitudinally on its tracks 68 and 69.

It will be evident from the description thus far, that when reversible motor 53 drives chain 81 in one direction or another, the subassembly 56 which mounts the film changer 50 for longitudinal translation will rotate but the other subassembly 54 which mounts it for vertical movements will not rotate and will stay aligned with the rear or base section 16 of the U-arm 15.

As can be seen in FIGS. 2 and 7, film changer 50 can be positioned very close to the head of a patient. One of the reasons for making the film changer movable longitudinally by small amounts is to enable it to be shifted far enough to clear the shoulder of a patient lying on X-ray table top 41 as shown in FIG. 7 when it is desired to make an unmagnified image of the patient's skull which requires that the image or film plane of the receptor be as close as possible to the skull. In FIG. 2, the X-ray source is on the right side of the patient and the film changer on the left. When it is desired to obtain a view from the opposite side of the patient, L-arm 10 is rotated about its vertical axis in which case the film changer would be on the right side of the patient and the X-ray source 54 on the left side. Longitudinal translation of the film changer off-center of the view arm axis 20 might again be required if it is desired to have the film changer in contact with the patient's skull.

As can be seen in FIG. 2, the film changer upright member or stand 51 is mounted for being translated away from the position of the patient in which it is presently shown to a greater distance such as to the limit against the base section 16 of the U-arm. In other words, a relatively long source-to-image distance can be obtained for procedures ranging from low magnification where the film changer is in contact with the patient to maximum magnification where the source-to-image distance is the greatest. Film changer 50 and X-ray source 54 can be set apart about 100 cm. which is the SID for standard magnification with the patient about midway between source and film plane, and the changer and source can be shifted in the same direction to hold the SID and yet obtain different amounts of magnification. To enable varying the distance between the patient and the image plane of the film changer, stand 51 is mounted for sliding on a pair of tracks 95 and 96 which are fastened to the top surface of axially extending section 18 of the U-arm as can be seen in FIG. 4 and FIGS. 3 and 2 as well. In FIG. 4, guides 97 and 98 are fastened to the bottom plate 99 of the stand 51 and they dovetail with the tracks 95 and 96 to permit sliding movement and yet prevent the film changer stand from falling off when the U-arm is tilted significantly. Stand 51 is moved manually on the tracks and may be provided with a lock, not shown, to secure it in a selected position on the tracks 95 and 96, although a lock is not absolutely necessary since U-arm section 18 is always horizontal regardless of how the U-arm is angulated relative to a patient on the table 41.

FIG. 7 illustrates longitudinal translation of film changer 50 for a procedure in which it is desired to have the film changer close to the patient's skull. One may see how it is moved from its normal position, shown in phantom, where its center is coincident with U-arm axis 20 to a solid line position where it clears the shoulder of the patient and is closer to the skull.

In summary, angiography apparatus has been described wherein a second film changer for lateral radiography is integrated into a gantry along with an X-ray source, a first film changer and an X-ray image intensifier for making PA views of a patient's blood vessels and associated anatomy. With few exceptions, all PA and lateral X-ray views of the patient are taken without the need for raising or lowering the patient with respect to isocenter 42. Variable X-ray source-to-image distances are obtainable with the PA viewing system and the lateral viewing system as well. The lateral film changer is mounted in a fashion which disposes it in an unobstructing attitude when required.

Although the apparatus has been described in considerable detail, such description is intended to be illustrative rather than limiting, for the inventive concepts may be variously implemented and are to be limited only by interpretation of the claims which follow.

We claim:

1. X-ray apparatus for bi-plane angiography comprising:
   support means movable about a vertical axis,
   a U-arm comprising a base section and means mounting said base section on said support means for rotation about a horizontal axis and said U-arm having leg sections, respectively, extending axially from the base section on opposite sides of the horizontal axis,
   an X-ray source mounted to one of the leg sections for projecting an X-ray beam along an axis perpendicular to the horizontal axis, the intersection of said vertical, horizontal and X-ray beam axes constituting an isocenter occurring in a region where a body is to be located for examination,
   carriage means mounted to the other of the leg sections for moving radially inwardly and outwardly relative to the horizontal axis,
   a first film changer mounted to said carriage means for presenting a radiographic film in planes determined by the radial position of said carriage means, said planes being intersected by the X-ray beam axis and being generally parallel to the horizontal axis, and
   a second film changer for making lateral X-ray views and means for mounting said changer to said U-arm between said leg sections and between said isocenter and base section for said second changer to present a radiographic film in a plane to which said horizontal axis is generally perpendicular.

2. The apparatus as in claim 1 wherein said mounting means for said second film changer includes means supporting said film changer for translating along said horizontal axis toward or away from said isocenter.

3. The apparatus as in any of claims 1 or 2 wherein said mounting means for the second film changer includes means supporting said film changer for rotation about said horizontal axis, and means for rotating said supporting means relative to the U-arm in a direction opposite to the direction in which the U-arm is rotated about the horizontal axis from vertical to thereby keep said second film changer level for at least a predetermined amount of U-arm rotation.

4. The apparatus as in any of claims 1 or 2 wherein said mounting means for the second film changer includes means supporting said film changer for rotation about said horizontal axis, and means for causing said supporting means to rotate in the same direction in which the U-arm is rotated when the U-arm is rotated about the horizontal axis, beyond a predetermined angle from vertical, thereby enabling said second film changer to avoid being struck by said first film changer.

5. The appratus as in claim 1 wherein said means for mounting the second film changer includes means supporting said film changer for rotation about said horizontal axis, means operative to cause said supporting means to rotate relative to the U-arm in an angular direction opposite from the angular direction in which the U-arm is rotated to thereby keep said second film changer level until said U-arm has been rotated to a predetermined angle from vertical and operative to enable said film changer supporting means to rotate in the same direction as said U-arm when it has rotated beyond said predetermined angle.

6. The apparatus as in claim 1 wherein said mounting means for said second film changer comprises:

a support member mounted to said one leg section for translating toward and away from said isocenter in a region between the U-arm base section and the isocenter, first means mounted to said support member for moving linearly in parallel with said base section and perpendicularly to the rotational axis of the U-arm, second means mounted for rotation on the first means, third means mounted for moving on the second means generally transversely to the line of movement of the first means, said film changer being mounted to said third means.

7. X-ray apparatus for bi-plane angiography, comprising:

an L-arm including an upstanding section and a horizontal section supported at one end for enabling the L-arm to rotate about a vertical axis, a U-arm comprising a base section and leg members extending in parallelism from opposite ends of the base section, said base section being mounted for rotation on the upstanding section of the L-arm for rotation about a horizontal axis with said members being on opposite sides of said axis, an X-ray source and means for mounting said source to one leg member for projecting an X-ray beam along an axis perpendicular to said horizontal axis and substantially coincident with said vertical axis, the intersection of said vertical, X-ray beam and horizontal axes constituting an isocenter occurring in a region where a body is to be located for examination, a first film changer supported from the other of said leg section for moving radially inwardly and outwardly relative to said isocenter and for moving in parallelism with the U-arm axis between an active position wherein said changer presents a radiographic film in planes intersected by said X-ray beam axis and an inactive position out of alignment with said X-ray beam axis, a second film changer for lateral radiography and means for mounting said changer within the space defined by said leg sections and base section of the U-arm for rotation about a horizontal axis and translation in planes to which said axis is perpendicular and for presenting a radiographic film in planes to which said axis of the U-arm is generally perpendicular.

8. The apparatus as in claim 7 wherein said mounting means for said second film changer includes means supporting said film changer for translating along said horizontal axis toward or away from said isocenter.

9. The apparatus as in any of claims 7 or 8 wherein said mounting means for the second film changer includes means supporting said film changer for rotation about said horizontal axis, and means for rotating said supporting means relative to the U-arm in a direction opposite to the direction in which the U-arm is rotated about the horizontal axis from vertical to thereby keep said second film changer level for at least a predetermined amount of U-arm rotation.

10. The apparatus as in any of claims 7 or 8 wherein said mounting means for the second film changer includes means supporting said film changer for rotation about said horizontal axis, and means for causing said supporting means to rotate in the same direction in which the U-arm is rotated when the U-arm is rotated about the horizontal axis, beyond a predetermined angle from vertical, thereby enabling said second film changer to avoid being struck by said first film changer.

11. The apparatus as in claim 7 wherein said means for mounting the second film changer includes means supporting said film changer for rotation about said horizontal axis, means operative to cause said supporting means to rotate relative to the U-arm in an angular direction opposite from the angular direction in which the U-arm is rotated to thereby keep said second film changer level until said U-arm has been rotated to a predetermined angle from vertical and operative to enable said film changer supporting means to rotate in the same direction as said U-arm when it has rotated beyond said predetermined angle.

12. The apparatus as in claim 7 wherein said mounting means for said second film changer comprises:

a support member mounted to said one leg section for translating toward and away from said isocenter in a region between the U-arm base section and the isocenter, first means mounted to said support member for moving linearly in parallel with said base section and perpendicularly to the rotational axis of the U-arm, second means mounted for rotation on the first means, third means mounted for moving on the second means generally transversely to the line of movement of the first means, said film changer being mounted to said third means.

* * * * *